US012642748B2

(12) United States Patent
Fabien

(10) Patent No.: US 12,642,748 B2
(45) Date of Patent: Jun. 2, 2026

(54) ASSEMBLY COMPRISING A FLUID PRODUCT DISPENSER AND AN UNLOCKING DEVICE

(71) Applicant: APTAR FRANCE SAS, Le Neubourg (FR)

(72) Inventor: David Fabien, Saint Renan (FR)

(73) Assignee: APTAR FRANCE SAS, Le Neubourg (FR)

( * ) Notice: Subject to any disclaimer, the term of this patent is extended or adjusted under 35 U.S.C. 154(b) by 148 days.

(21) Appl. No.: 18/727,947

(22) PCT Filed: Jan. 9, 2023

(86) PCT No.: PCT/FR2023/050020
§ 371 (c)(1),
(2) Date: Jul. 10, 2024

(87) PCT Pub. No.: WO2023/135383
PCT Pub. Date: Jul. 20, 2023

(65) Prior Publication Data
US 2025/0099337 A1 Mar. 27, 2025

(30) Foreign Application Priority Data
Jan. 11, 2022 (FR) ...................................... 2200188

(51) Int. Cl.
*A61J 7/00* (2006.01)
*A61M 15/00* (2006.01)
(52) U.S. Cl.
CPC ........ *A61J 7/0053* (2013.01); *A61M 15/0081* (2014.02)

(58) Field of Classification Search
CPC ............ A61J 7/0053; A61J 1/065; A61J 1/16; A61M 15/0081; A61M 2205/10;
(Continued)

(56) References Cited

U.S. PATENT DOCUMENTS 5,692,492 A 12/1997 Bruna et al.
8,640,694 B2 * 2/2014 Fabien .............. A61M 15/0045
128/203.15

(Continued)

FOREIGN PATENT DOCUMENTS

DE 202010005002 U1 8/2011
EP 0071931 A2 2/1983
(Continued)

OTHER PUBLICATIONS

International Search Report for PCT/FR2023/050020 dated Apr. 20, 2023.
(Continued)

*Primary Examiner* — Donnell A Long
(74) *Attorney, Agent, or Firm* — Sughrue Mion, PLLC

(57) ABSTRACT

Assembly having a fluid product dispenser and an unlocking device. The assembly has a fluid product dispenser (D) having a movable member (F) and a locking system (L) that is switchable between a locking position, in which the movable member (F) is locked and a release position, in which the movable member (F) is unlocked; and an unlocking device (K), separate from the fluid product dispenser (D), that is able to switch the locking system (L) between the locking position and the release position, this unlocking device (K) being an eddy-current-based contactless and remote unlocking device.

9 Claims, 5 Drawing Sheets

Figures 1, 2:
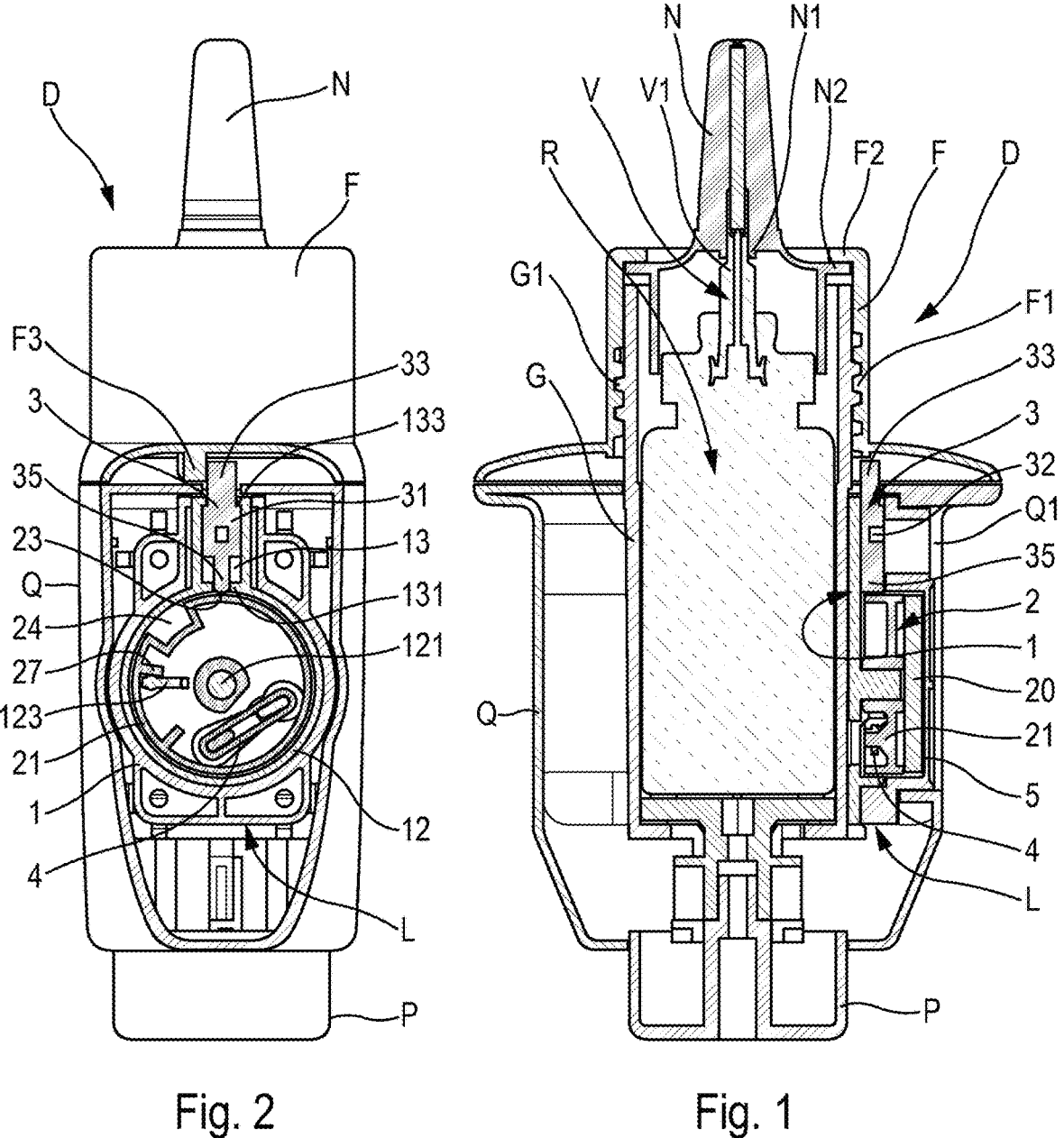

(58) Field of Classification Search
CPC .............. A61M 2205/27; A61M 15/08; A61M
11/007; B05B 11/1059; B65D 50/061;
B65D 50/06
See application file for complete search history.

(56) References Cited

U.S. PATENT DOCUMENTS

| | | | | |
|---|---|---|---|---|
| 2007/0205902 A1* | 9/2007 | Cote | ...................... | G01V 15/00 |
| | | | | 340/572.9 |
| 2019/0134322 A1* | 5/2019 | Fabien | ................ | A61M 15/009 |
| 2020/0246562 A1* | 8/2020 | Fabien | ................ | A61M 15/008 |
| 2021/0187210 A1* | 6/2021 | Brouet | ................ | A61M 15/009 |
| 2021/0187215 A1* | 6/2021 | Fabien | .............. | A61M 15/0091 |

FOREIGN PATENT DOCUMENTS

| | | | |
|---|---|---|---|
| EP | 2436415 | A1 | 4/2012 |
| WO | 01/93932 | A1 | 12/2001 |
| WO | 2018/058287 | A1 | 4/2018 |
| WO | 2021/084092 | A1 | 5/2021 |

OTHER PUBLICATIONS

International Preliminary Report on Patentability dated Apr. 19, 2024 of the International Searching Authority in Application No. PCT/FR2023/050020.

* cited by examiner

ASSEMBLY COMPRISING A FLUID PRODUCT DISPENSER AND AN UNLOCKING DEVICE

CROSS REFERENCE TO RELATED APPLICATIONS

This application is a National Stage of International Application No. PCT/FR2023/050020 filed Jan. 9, 2023, claiming priority based on French Patent Application No. 2200188 filed Jan. 11, 2022.

The present invention relates to an assembly comprising two separate entities, adapted to be added, one on or in contact with the other, in order to engage to generate an unlocking operation, these two entities including, on the one hand, a fluid product dispenser comprising a movable member and a locking system that is switchable between a locking position, in which the movable member is locked and a release position, in which the movable member is unlocked, and on the other hand, an unlocking device, separate from the dispenser, that is able to switch the locking system between the locking position and the release position. The favoured field of application of this invention is that of pharmacy, without, however, excluding other fields, like those of perfumery, cosmetics or even drugstores.

In a figurative way, it can be said that the dispenser integrates a latch locking one of its functions, and that the unlocking device is a type of key which makes it possible to actuate the latch, in order to release the function of the dispenser. This function can be of any nature, but always controlled by a movable member, which makes it possible, for example, to access a component of the dispenser or to enable the operation of the dispenser. The movable member can be a cap, a cover, a shutter, a bottom or also a part of a mechanism involved in the dispensing of the fluid product. The movable member can enable access to a reservoir, for example, equipped with a dispensing member, like a pump, a valve or a simple stopper. The movable member can make it possible to control the dosage (time between two times taking medication). The nature and the function of the movable member is not critical for the present invention, insofar as its locking prevents an unindicated use of the dispenser.

In the field of pharmacy, for example, the administration of powerful substances which are potentially lethal to human beings can be a necessity in certain situations. This is particularly the case for the treatment of particular diseases, or indeed for people in need of palliative treatment in end-of-life contexts.

Handling such substances requires great caution and extremely safe administration devices in order to avoid the risks of overdose, which can occur in case of a number of consecutive doses which is too high.

A risk is also present, which relates to the use of devices by a person other than the person to whom the treatment is intended (children, for example).

In this context, the aim of the invention is to develop a secure dispenser/unlocking device assembly to avoid risks of overdose, and usable only by the person in need. Thus, only the person having this dedicated unlocking device can use the dispenser. The unlocking device can be used in a factory or by an authorised entity, like a pharmacist or a doctor.

In the prior art, unlocking devices are already known, making it possible to deactivate or neutralise magnetic anti-theft devices, like those that are used in shops, for example, for clothes. This type of magnetic anti-theft device can be easily deactivated by means of a simple permanent magnet which is added to the anti-theft device, such that it is not secure.

Also, numerous locking systems are known which can be deactivated by means of a specific key, which acts mechanically on the locking system. The disadvantage of these mechanical systems is that they can be seen and can therefore form the subject of intrusion attempts, which can lead to the opening of the locking system or to it being damaged.

Thus, magnetic anti-theft devices are inaccessible, but too simple to deactivate and mechanical anti-theft devices are more difficult to deactivate, but too accessible.

The present invention aims to overcome the disadvantages of the locking systems of the prior art, by cumulating their advantages and by removing their disadvantages. The locking system of the invention must be both inaccessible and difficult to deactivate. To do this, the present invention proposes an assembly comprising:

fluid product dispenser comprising a movable member and a locking system that is switchable between a locking position, in which the movable member is locked and a release position, in which the movable member is unlocked, an unlocking device, separate from the dispenser, that is able to switch the locking system between the locking position and the release position, this unlocking device being an eddy-current-based contactless and remote unlocking device. Instead of using simple magnetic attraction, like in a conventional magnetic anti-theft device, the present invention uses an electromagnetic principle based on eddy currents and Lenz-Faraday law.

Electric currents created in a conductive ground, either by variation over time of an external magnetic field passing through this medium (the flow of the field through the medium), or by a movement of this ground in a magnetic field, are called "eddy currents". They are a consequence of electromagnetic induction.

When the flow variation is due to a movement of the medium in front of a constant magnetic field, eddy currents are responsible for the appearance of laplace forces which oppose the movement, hence the braking effect observed on the systems using this type of device.

The Laplace forces, created by this induced current phenomenon, oppose the cause which has given them the effect, i.e. the rotation of the magnet(s) about the axis.

To oppose this relative rotary movement, the Laplace forces therefore take the form of a torque on the induction disc aiming to rotate the disc in the same direction of rotation as the axis of the magnets in order to reduce these currents.

In physics, Lenz-Faraday law, or Faraday's law, makes it possible to reflect electromagnetic induction macroscopic phenomena. The direction of the induced current (oriented in the same direction as the induced electric field) is such that this always tends to oppose, by its effects, the cause which has produced it:

in the case of a variable magnetic field, the field created by the induced current itself opposes the variation of the initial field, in the case of a movable circuit, the Laplace forces due to the induced current oppose the initial movement of the circuit.

This interpretation is known as Lenz's moderation law.

Advantageously, the locking system can comprise a movable induction element and the unlocking device comprises variable magnetic field generation means inducing an electromotive force on the movable induction element which makes it possible to switch the locking system from its locking position to its release position. The induction element can be rotatably, translatably or pivotingly moved, according to the nature of the variable magnetic field. An anti-magnetic conductive slider can very well be designed, which is translatably moved so as to release the movable member.

According to a practical embodiment, the movable induction element can be an induction disc, rotating about an axis X and the variable magnetic field generation means comprise at least one permanent magnet rotated about an axis Y or a set of solenoids disposed about an axis Y and alternately powered so as to produce a rotating magnetic field, the axes X and Y being aligned when the unlocking device is added to the dispenser or vice versa, such that the variable magnetic field generation means thus induce a rotary movement to the induction disc from a rest position to an active position.

Compared with the lorry braking system, in which the induction disc rotates and static magnets slow down the rotation of the induction disc, in the present invention, the magnets rotate and cause the induction disc which is static at rest to rotate.

Advantageously, the induction disc is urged into the rest position by resilient means. Thus, it is not necessary to use the unlocking device to return the induction disc into the initial rest position. Preferably, the induction disc can comprise at least one abutment profile to limit its rotation between the rest position and the active position.

The induction disc can itself alone or almost constitute the locking system and act directly on the movable member, but preferably, the locking system further comprises a catch that is movable between an interposition position in which the catch locks the movable member and a release position in which the movable member is unlocked, the catch being locked in the interposition position by the induction disc in the rest position and movable in the release position when the induction disc is in the active position urged by the variable magnetic field generation means.

Advantageously, the movement of the catch is translative, a movement member being provided to engage with the movable catch to move it translatably from its interposition position to its release position, this movement member being advantageously integrated in the unlocking device in the form of a pivoting lever. In a variant, the catch can be rotary or pivoting. It can also be connected to the induction disc, for example by a connecting rod.

According to a practical embodiment, the induction disc in the rest position can comprise an abutment wall which locks the movable catch in its interposition position, the induction disc in the active position comprising a housing which receives the catch translatably moved into its release position by the movement member. Preferably, the catch can comprise an interposition head, an axial guiding body and an abutment stub, the interposition head coming into contact with the removable closing element to lock it, the abutment stub coming into contact with the abutment wall or in position in the housing, the axial guiding body advantageously forming a gripping profile for the movement member.

According to another aspect of the invention, the fluid product dispenser can comprise a support plate forming a receiving frame for the induction disc and an axial guiding funnel for the catch, the axial guiding funnel opening into the frame, the receiving frame being advantageously provided with a rod defining the axis of rotation X for the induction disc, with a hook for the resilient means urging the induction disc into the rest position and a stop to limit the rotation of the induction disc.

According to a preferred embodiment, the unlocking device can comprise several permanent magnets disposed parallel with an alternate polarity about an axis of rotation Y, the unlocking device comprising axis alignment means that are able to favour the alignment of the two axes X and Y, when the fluid product dispenser is added to the unlocking device or vice versa, the unlocking device comprising or being associated with a motor to drive the permanent magnets about the axis Y, the motor rotating advantageously at least 200 rotations per minute, and preferably at around 300 rotations per minute.

The spirit of the invention resides in the fact of moving an induction element, which is made of an anti-magnetic conductive material, by means of a variable magnetic field created by an unlocking device, which is separate from the dispenser.

The invention is now described more fully below with reference to the accompanying drawings, which show an embodiment of the invention by way of non-limiting example.

Figure 3:
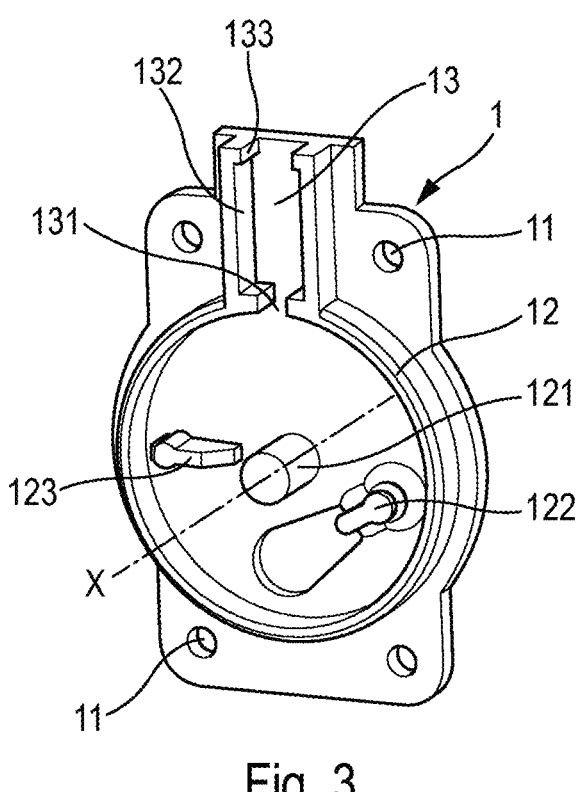
Figure 4:
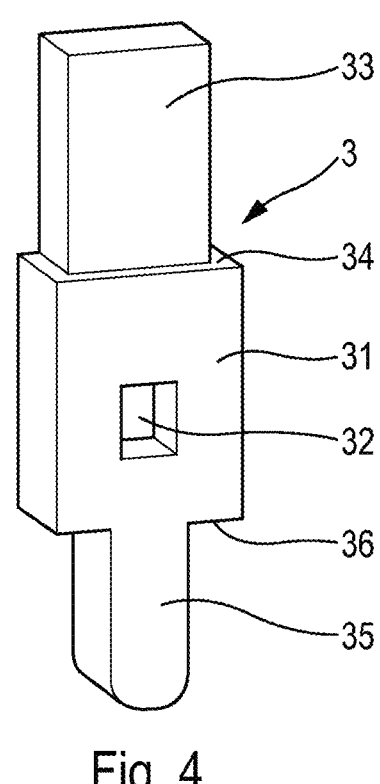
Figure 5A:
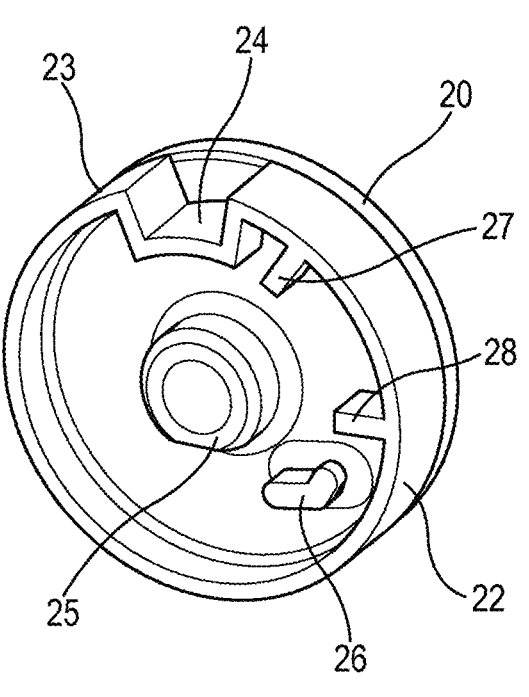
Figure 5B:
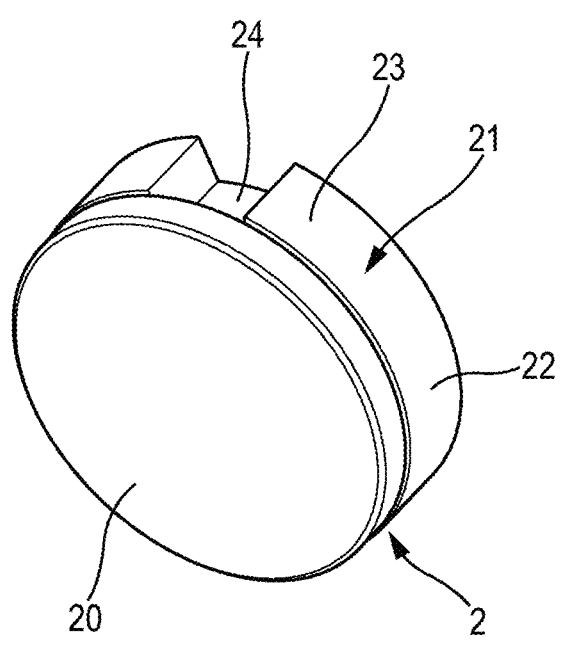
Figure 6A:
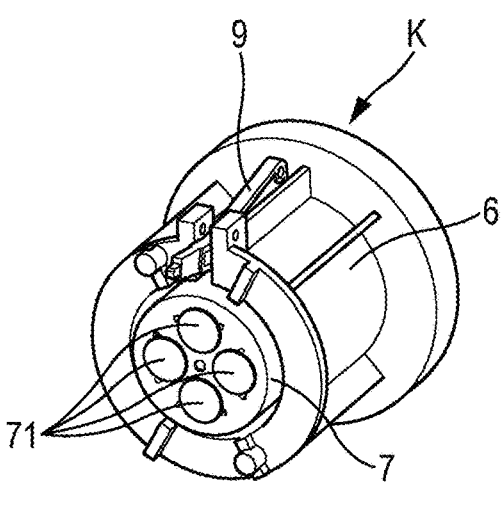
Figure 6B:
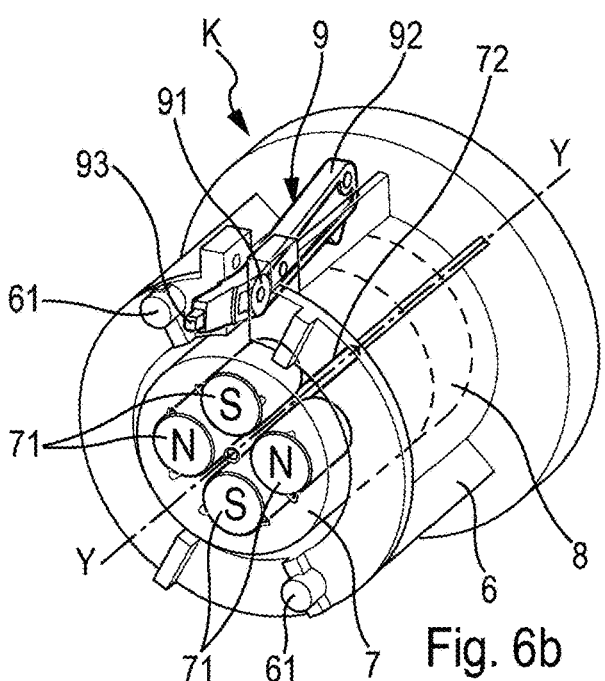
Figure 6C:
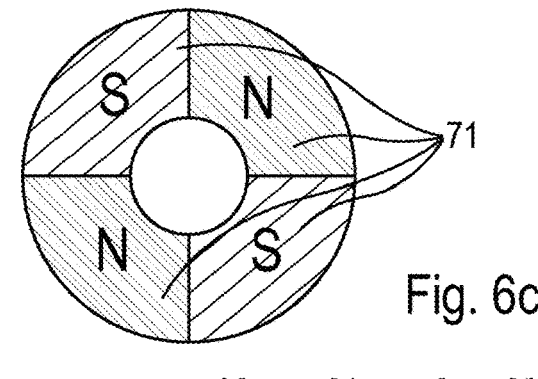
Figure 7:
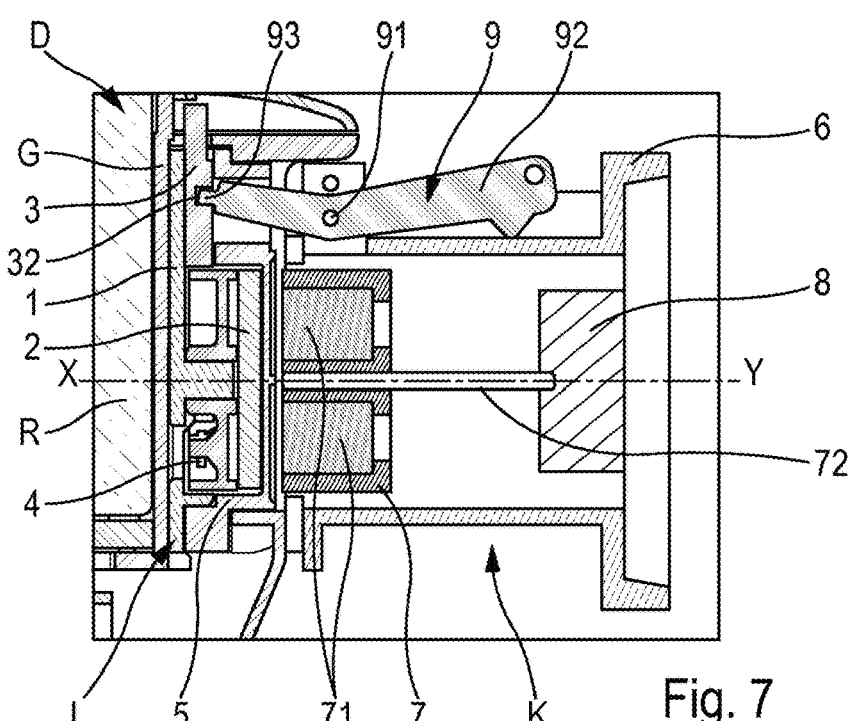
Figures 8A, 8B:
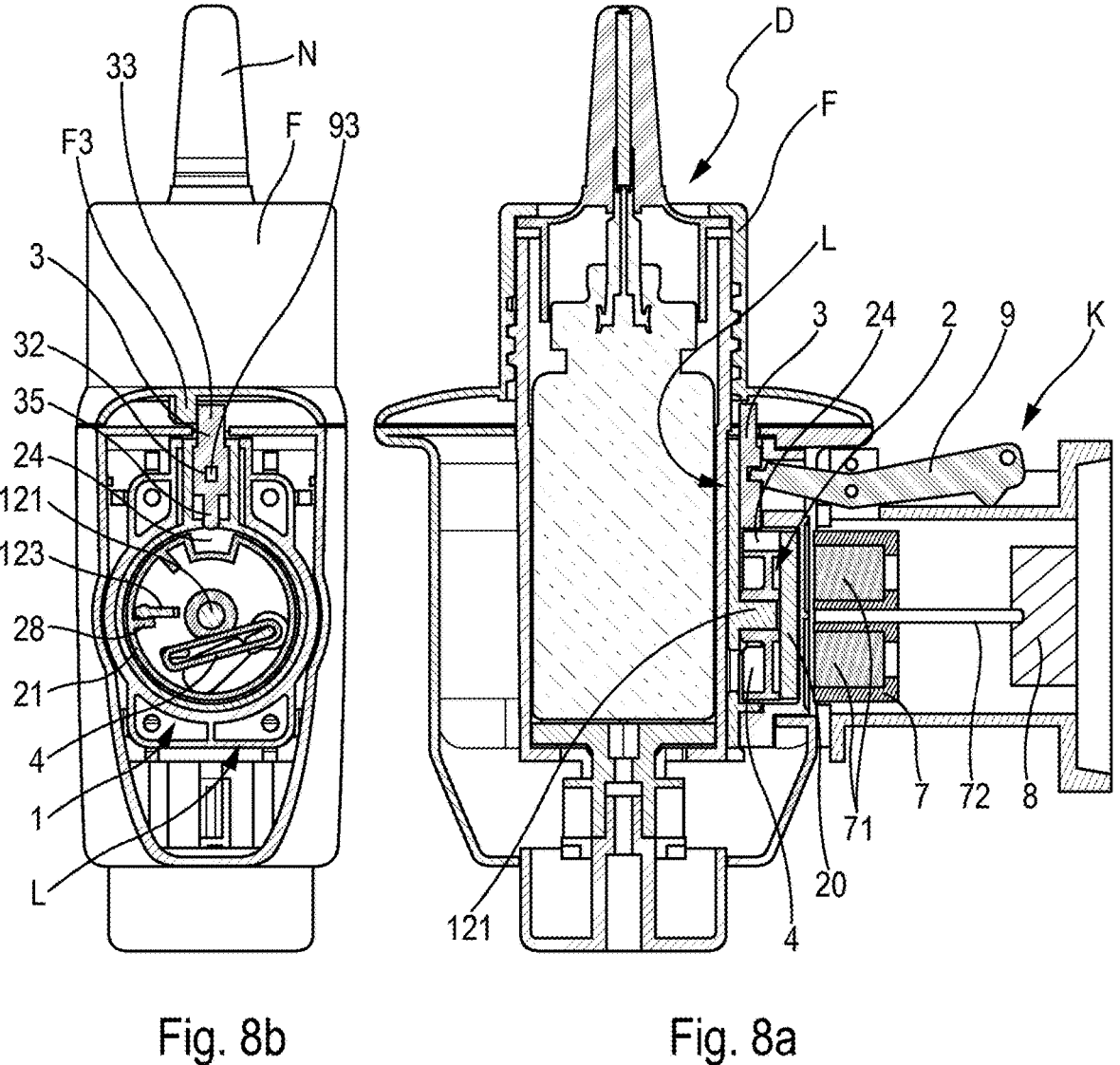
Figures 9A, 9B, 10:
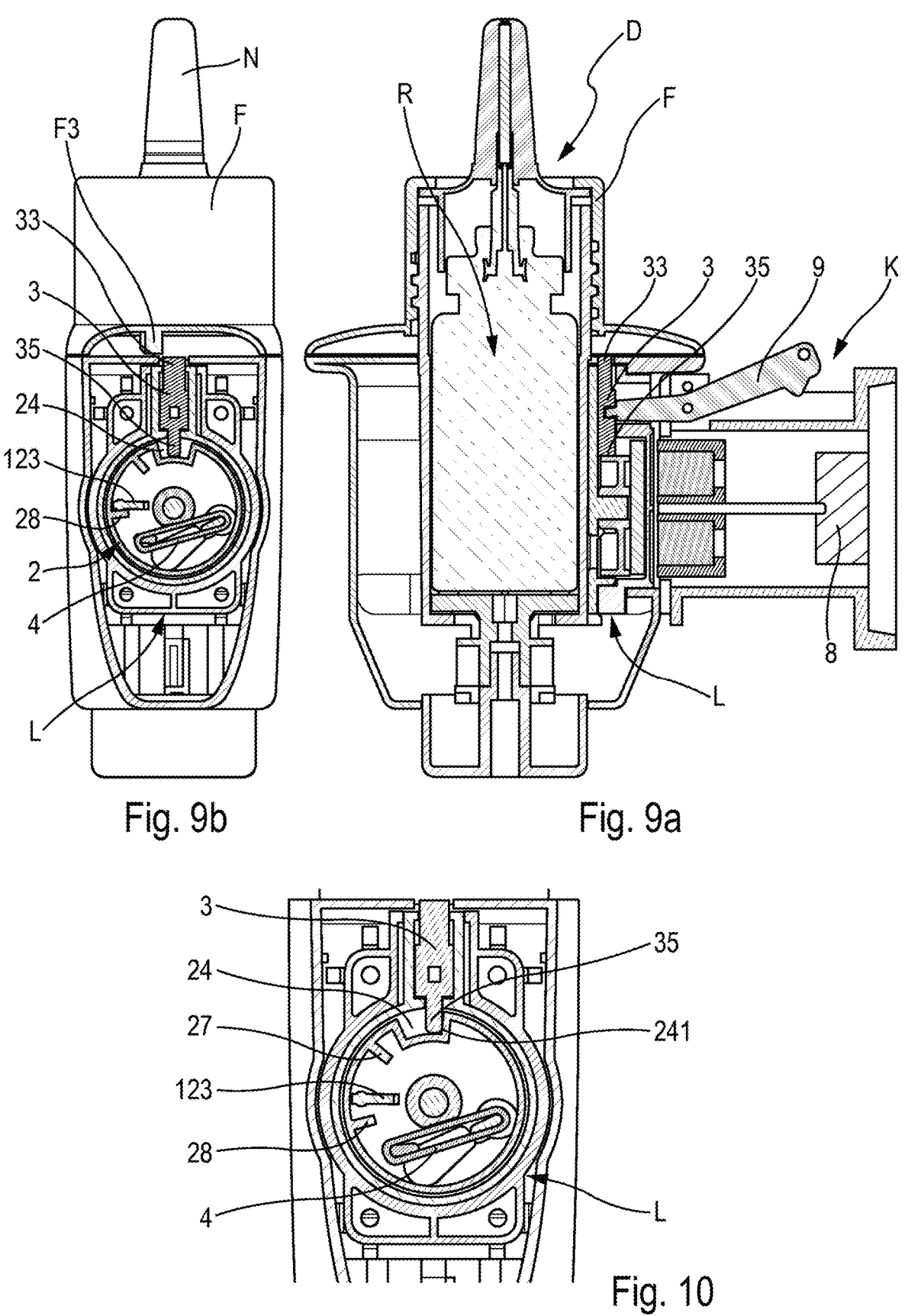

In the figures:

FIG. 1 is a vertical cross-sectional view through a fluid product dispenser according to the invention, FIG. 2 is a partially cross-sectional side view of the fluid product dispenser of FIG. 1, FIG. 3 is an enlarged perspective view of the support plate of the dispenser of FIGS. 1 and 2, FIG. 4 is a very highly enlarged perspective view of the catch of the dispenser of FIGS. 1 and 2, FIGS. 5a and 5b are front and back enlarged perspective views of the induction disc of the dispenser of FIGS. 1 and 2, FIG. 6a is a perspective view of an unlocking device according to the invention, FIG. 6b is a perspective and partially transparent view of the unlocking device of FIG. 6a, FIG. 6c is a schematic representation aiming to illustrate a particular configuration for the magnets of the unlocking device of FIGS. 6a and 6b, FIG. 7 is a vertical cross-sectional view through the unlocking device of FIGS. 6a and 6b associated with the dispenser of FIGS. 1 and 2, FIGS. 8a and 8b are views similar to FIGS. 1 and 2 with the unlocking device of FIGS. 6a and 6b acting on the dispenser, FIGS. 9a and 9b are views similar to those of FIGS. 8a and 8b, with the unlocking device fully actuated, and FIG. 10 is an enlarged view similar to FIGS. 8b and 9b showing the dispenser in a configuration that is able to remove the cap from the dispenser.

Reference is made firstly to FIGS. 1 and 2 in order to describe the general structure of a fluid product dispenser D according to the invention. Reference is then made to FIGS. 6a, 6b, 6c and 7 in order to describe the unlocking device K of the invention, which is intended to be associated with the fluid product dispenser D to unlock it and thus enable an operation.

The fluid product dispenser D of FIGS. 1 and 2 is a nasal dispenser intended to inject the fluid product, dosed or not, into a nostril of a patient. This is only a particular example, which is not limiting, in any case. Any other type of fluid product dispenser could be used in the scope of the present invention. Thus, the dispenser D comprises a fluid product reservoir R which is, in this case, equipped with a dispensing valve V. Instead of the valve V, a pump or any other dispensing device could also be used. The valve V is capped with a nasal endpiece N intended to be inserted into the nostril of the patient. The nasal endpiece N comprises a connecting sleeve N1 which is engaged around the free end of the valve rod V1 of the valve V. The nasal endpiece N also comprises an annular holding collar N2 which makes it possible to fixedly hold the nasal endpiece N, as can be seen below. The reservoir R is disposed inside a sheath G with an external thread G1 in its upper part. The sheath G is open at its lower end for the passage of a pushbutton P. A closing cap F is formed with a thread F1 and an upper inwardly-directed flap F2. The internal thread F1 is intended to threadingly engage with the external thread G1 of the sheath G. When the cap F is fully screwed on the sheath G, its upper inwardly-directed flap F2 engages with the annular holding collar N2 of the nasal endpiece N and thus holds it fixedly in place.

It is already understood that an actuation of the pushbutton P will move the reservoir R inside the sheath G by leaving the nasal endpiece N static. In doing so, the valve V is stressed in its open state, which makes it possible for the fluid product stored in the reservoir R to be discharged through the valve V and the nasal endpiece N. This is an absolutely conventional operation for a nasal dispenser. It is also understood that it is possible to access the reservoir R inside the sheath G by unscrewing the closing cap F. Its replacement or the insertion of a different reservoir can thus be proceeded with.

The dispenser D also comprises a shell Q which partially surrounds the sheath G, leaves a passage for the pushbutton P and also serves as a docking surface for the closing cap F. This external shell Q comprises a side window Q1, the function of which will be given below.

This dispenser D is, for the time being, an absolutely conventional design, but it further incorporates a locking system L, which forms part of the invention.

It can be noted that the dispenser D comprises a support plate 1, which is mounted on a side wall of the sheath G. This support plate 1 serves as a support for an induction disc 2, as well as a catch 3. A cover 5 is mounted on the support plate 1 by fully covering the induction disc 2 and by leaving access to the catch 3. The cover 5 is mounted in the side window Q1 of the shell Q.

In FIG. 2, it can be noted that the catch 3 comprises an interposition head 33, against which a locking lug F3 formed by the screwable closing cap F abuts. It is easily understood that the interposition of the head 33 prevents the unscrewing of the cap F. The dispenser D is therefore in a locking configuration, in which it is impossible to access the reservoir R.

FIGS. 3, 4, 5a and 5b will now be referred to, to describe, in detail, the structure of the support plate 1, of the induction disc 2 and of the catch 3, which together constitute the main part of the locking system L of the invention.

In FIG. 3, it can be seen that the support plate 1 comprises several fixing holes 11, which enable it to be mounted on the sheath G, or more generally on a fixed structure of the dispenser D. The support plate 1 forms an annular-shaped receiving frame 12, which communicates by a reduced lower passage 131 with a vertical funnel 13, defining two opposite side walls 133 and ending by a reduced upper outlet 133. The frame 12 internally forms a rod 121 defining an axis of rotation X, a hook 122 for a spring 4, as well as a stop 123, which extends substantially radially. The support plate 1 can conventionally be made by injection moulding a plastic material.

In FIGS. 5a and 5b, it can be seen that the induction disc 2 comprises, in this particular embodiment, two separate parts which are secured to one another, namely a patch 20 made of an anti-magnetic conductive material and a wheel 21 which can be made by injection moulding a plastic material. In a variant, it is also possible to make the induction disc 2 of one piece, for example by moulding or pressing of an anti-magnetic conductive material, such as copper or aluminium. In this particular embodiment, the patch 20 can be substantially cylindrically-shaped with a flat edge face and parallel opposite flat faces. The patch 20 can, for example, be glued or snap-fitted on the wheel 21. The wheel 21 comprises a substantially cylindrical rim 22, which is interrupted at a housing 24. Internally, the rim 22 forms two abutment profiles 27 and 28, which extend substantially radially inwards from the rim 22. The wheel 21 also forms an anchoring 26 for a return spring 4, as can be seen below. Finally, the wheel 22 forms a hub 25 in its centre. It can be noted that the diameter of the patch 20 corresponds substantially to the diameter of the rim 22 of the wheel 21. Only the housing 24 interrupts the rim 22.

In FIG. 4, it can be seen that the catch 3 is a one-piece part, which can, for example, be made by injection moulding a plastic material. The catch 3 comprises an axial guiding body 31 which is formed with a gripping profile 32 which is presented in the form of a recess. At its upper end, the guiding body is extended by the interposition head 33 mentioned above. It can be noted that an upper shoulder 34 makes the junction between the body 31 and the head 33. In an opposite manner, the body 31 is extended downwards by an abutment stub 35. Again, a lower shoulder 36 forms the junction between the body 31 and the stub 35.

These three parts of the locking system L now being described, FIGS. 1 and 2 are returned to, to explain their arrangement and engagement within the dispenser D. First, it can be noted that the support plate 1 is fixed on the side wall of the sheath G. Then, it can be seen that the induction disc 2 is mounted in the frame 12 of the plate 1. The diameter of the induction disc 2 can be slightly less than that of the frame 12, so as to reduce both the clearances and the friction. The hub 25 of the wheel 21 is engaged around the rod 121 of the plate 1. The stop 123 is engaged between the two abutment profiles 27 and 28, so as to limit the angular stroke of the induction disc 2 in the frame 12. A spring 4, for example, in the form of a resilient loop or a coil spring, is engaged around the anchoring 26 and the hook 122 of the plate 1. This spring 4 urges the induction disc 2 anti-clockwise, such that the abutment profile 27 bears against the line 123. This can be seen in FIG. 2.

Regarding the catch, it can be seen that its interposition head 33 is located adjacent to the locking lug F3 of the cap F to be screwed. This body 31 is engaged in the funnel 13 between the two side walls 132 and between the two reduced passages 131 and 133. It can thus be said that the funnel 13 confines the catch 3, while being able to be translatably moved between the two reduced passages 131 and 133. The interposition head 33 extends through the reduced upper passage 133 and the abutment stub 35 extends through the reduced lower passage 131. It can be noted in FIGS. 1 and 2, that the lower end of the abutment stub 35 is in contact with the rim 22 of the wheel 21 in a point 23 which is located in the proximity of the housing 24. In this locking position, the upper shoulder 34 abuts against the reduced upper passage 133, while the lower shoulder 35 remains remote from the reduced lower passage 131. The catch 3 is therefore fully fixed in this so-called locking position. The unscrewing the closing cap F is prevented by the abutting of the lug F3 against the interposition head 33 of the catch 3. The user cannot access the reservoir R to replace it.

By referring to FIGS. 6*a* and 6*b*, the unlocking device K of the invention can be seen, which makes it possible to rotate the induction disc 2 over a limited angle, however making it possible to bring the housing 24 to face the abutment stub 35 of the catch 3. This unlocking device K comprises a body 6, which can be made by injection moulding a plastic material. This body 6 presents a general configuration that is substantially cylindrical with a through inside. The body 6 contains a rotor 7 supporting several permanent magnets 71, advantageously disposed with alternate polarities. The rotor 7 is mounted on a shaft 72, which can be rotated by a motor 8. In a minimalist version, the rotor 7 could only comprise one single magnet, disposed in off-centre manner with respect to the shaft 72, which defines an axis of rotation Y. In this more optimised version, the four magnets 71 are disposed parallel to the shaft 72, but with alternate polarities, represented by the capital letters N and S. The magnets 71 can be presented in the form of small, cylindrical studs disposed side-by-side around the shaft 72. In an even more optimised variant represented in FIG. 6*c*, the four magnets 71 can be presented in the form of quarters disposed adjacently and together forming a disc with a central opening for the passage of the shaft 72. Without moving away from the scope of the invention, more than four magnets 71, for example six to twelve magnets, can naturally be imagined. It is understood that the motor 8 has the function of rotating the shaft 72, thus rotating the rotor 7 with its magnets 71 about the axis of rotation Y. Instead of the motor 8, of the rotor 7 with its magnets 71 and its shaft 72, a set of solenoids can be used, for example four or six of them, disposed about the axis Y and powered alternately (+/−) so as to produce a rotating magnetic field. This alternative embodiment makes it possible to avoid the use of a motor and of a rotor.

The body 6 is advantageously provided with alignment pins 61 which are disposed around the rotor. Their function is to favour the positioning of the unlocking device K with respect to the dispenser D, or vice versa.

Optionally, the unlocking device K also comprises a movement member 9, which will make it possible to translatably move the catch 3 in its funnel 13, when its abutment stub 35 will be disposed facing the housing 24 of the induction disc 2, as can be seen below. This movement member 9 can, for example, be presented in the form of a lever which can tilt about a pivot axis 91. The lever comprises an actuation part 92, as well as an engagement part forming an insertion nose 93, adapted to be inserted in the recess 32 of the catch 3. This movement means 9 could also be distinct and separated from the unlocking device K.

In FIG. 7, the unlocking device K is associated with the dispenser D, in an arrangement such that the axes of rotation X and Y are aligned and now combined. The alignment of these axes is favoured by the engagement of the alignment pins 61 of the body 6 of the corresponding housings of the dispenser D, for example at the cover 5. The rotor 7 is almost in contact with the cover 5, such that the magnets 71 are disposed in the proximity of the induction disc 2, so as to optimise the action of the magnets 71 on the disc 2. The nose 93 of the lever 9 is engaged inside the recess 32 of the catch 3. The motor 8 is not yet activated, such that the induction disc 2 is in the position represented in FIG. 2, with the abutment stub 35 of the catch 3 in contact with the rim 22 of the wheel 21 at the point 23.

FIGS. 8*a* and 8*b* illustrate the configuration of the dispenser D when the magnets 71 are rotated by the rotor 7 clockwise. As explained above, the rotation of the rotor 7 generates a variable magnetic field which will generate an electromotive force on the induction disc 2, or more specifically, on its anti-magnetic conductive patch 20. The induction disc 2 will thus be rotated clockwise, against the force exerted by the spring 4 in order to reach the configuration represented in FIG. 8*b*. It can be seen that the housing 24 is now located just below the abutment stub 35 and that the abutment profile 28 is in contact with the stop 123. The cap F is however also rotatably locked due to the interposition of the head 33 of the catch 3.

The torque generated on the induction disc 2 by the rotation of the rotor 7 is dependent on numerous parameters, like for example:

the magnetic field created by each magnet 71, which depends on its quality, the number of magnets 71, the arrangement of the magnets 71 on the rotor 7, the geometry of the magnets, the thickness of the patch 20, the electric resistivity of the material of the induction disc, the best being copper, or also the distance between the surface of the induction disc 2 and the magnets 71.

In order to create a sufficient torque on the induction disc 2, it is necessary that the rotor 7 rotates at a high speed: at least 200 rotations per minute, and preferably 300 rotations per minute, even by optimising all the parameters listed above. This necessary high rotation speed also contributes to and reinforces the tamper-proofing of the locking system.

In FIGS. 9*a* and 9*b*, it can be seen that the lever 9 has been actuated, so as to move the catch 3 between translation downwards to the inside of its funnel 13. The abutment stub 35 is now engaged inside the housing 24 and the interposition head 33 is now disposed below the locking lug F3. The motor 8 is always powered so as to preserve the angular orientation of the induction disc 2. However, from the engagement of the abutment stub 35 inside the housing 24, the power supply of the motor 8 can be cut off, which urges the induction disc 2 anti-clockwise over a very short stroke, since the abutment stub 35 will abut against a side wall 241 of the housing 24, as represented in FIG. 10, under the action of the spring 4.

Subsequently, the cap F can be unscrewed and the reservoir R can be replaced by another of the same type or of a different type. The cap F can then be put back in place by screwing on the sheath G. To finish, the catch 3 can be moved in its locking configuration of FIG. 2, using the lever 9 or using another utensil.

Although the invention has been described in reference to a closing cap to be screwed, the locking system L of the invention acting on any movable member of a dispenser can very well be imagined, that this member rotatably or translatably moves. The locking system L of the invention, which is constituted, in this case, by the plate 1, the induction disc 2, the catch 3 and the spring 4, can, in other embodiments, be reduced to a plate and to a rotary induction disc, which acts directly on the movable member, or also to a plate and a translatably movable induction catch, which acts directly on the movable member.

Without moving away from the scope of the invention, the support plate could be integrated in a part of the dispenser, like for example, the sheath G. The movement member 9 could be actuated by a motor. Instead of two abutment profiles 27 and 28 on the induction disc 2 and a stop 123 on the plate 1, an abutment profile on the disc and two stops on the plate can be provided.

Thanks to the invention, a dispenser is available, the locking system of which is inaccessible and totally incomprehensible, and the unlocking device of which implements less common specific electromagnetic means.

The invention claimed is:

1. An assembly comprising:

a fluid product dispenser comprising a movable member and a locking system that is switchable between a locking position, in which the movable member is locked and a release position, in which the movable member is unlocked, an unlocking device, separate from the fluid product dispenser, that is able to switch the locking system between the locking position and the release position, this unlocking device being an eddy-current-based contactless and remote unlocking device, wherein the locking system comprises a movable induction element and the unlocking device comprises variable magnetic field generation means inducing an electromotive force on the movable induction element which makes it possible to switch the locking system from its locking position to its release position, wherein the movable induction element is an induction disc rotating about an axis X and the variable magnetic field generation means comprise at least one permanent magnet rotated about an axis Y or a set of solenoids disposed about an axis Y and alternately powered so as to produce a rotating magnetic field, the axes X and Y being aligned when the unlocking device is added to the fluid product dispenser or vice versa, such that the variable magnetic field generation means thus induce a rotary movement to the induction disc from a rest position to an active position.

2. The assembly according to claim 1, wherein the induction disc is urged into the rest position by resilient means.

3. The assembly according to claim 1, wherein the induction disc comprises at least one abutment profile to limit its rotation between the rest position and the active position.

4. The assembly according to claim 1, wherein the locking system further comprises a catch that is movable between an interposition position in which the catch locks the movable member and a release position in which the movable member is unlocked, the catch being locked in the interposition position by the induction disc in the rest position and movable in the release position when the induction disc is in the active position urged by the variable magnetic field generation means.

5. The assembly according to claim 4, wherein the movement of the catch is translative, a movement member being provided to engage with the catch to move it translatably from its interposition position to its release position, this movement member being advantageously integrated in the unlocking device in the form of a pivoting lever.

6. The assembly according to claim 4, wherein the induction disc in the rest position comprises an abutment wall which locks the catch in its interposition position, the induction disc in the active position comprising a housing which receives the catch translatably moved into its release position by the movement member.

7. The assembly according to claim 6, wherein the catch comprises an interposition head, an axial guiding body and an abutment stub, the interposition head coming into contact with the movable member to lock it, the abutment stub coming into contact with the abutment wall or in position in the housing, the axial guiding body advantageously forming a gripping profile for the movement member.

8. The assembly according to claim 4, wherein the fluid product dispenser comprises a support plate forming a receiving frame for the induction disc and an axial guiding funnel for the catch, the axial guiding funnel opening into the receiving frame, the receiving frame being advantageously provided with a rod defining the axis of rotation X for the induction disc, with a hook for the resilient means urging the induction disc into the rest position and a stop to limit the rotation of the induction disc.

9. The assembly according to claim 1, wherein the unlocking device comprises several permanent magnets disposed alternately parallel in polarity about an axis of rotation Y, the unlocking device comprising axis alignment means that are able to favour the alignment of the two axes X and Y, when the fluid product dispenser is added to the unlocking device or vice versa, the unlocking device comprising a motor to drive the permanent magnets about the axis Y, the motor rotating advantageously at least 200 rotations per minute, and preferably at around 300 rotations per minute.

* * * * *